United States Patent [19]

Stamato et al.

[11] Patent Number: 4,830,726

[45] Date of Patent: May 16, 1989

[54] SEPARATION OF LARGE DNA MOLECULES IN ALTERNATING ASYMMETRIC ELECTRIC FIELDS

[75] Inventors: Thomas D. Stamato, Medford, N.J.; Nicholas Denko, Philadelphia, Pa.

[73] Assignee: The Wistar Institute, Philadelphia, Pa.

[21] Appl. No.: 151,651

[22] Filed: Feb. 3, 1988

[51] Int. Cl.$^4$ .............................................. G01N 27/26
[52] U.S. Cl. ................................................ 204/299 R
[58] Field of Search ................................... 204/299 R

[56] References Cited

U.S. PATENT DOCUMENTS 4,473,452  9/1987  Cantor ........................... 204/299 R

FOREIGN PATENT DOCUMENTS

87/00635  1/1987  PCT Int'l Appl. ............. 204/299 R

OTHER PUBLICATIONS

Schwartz et al., "Separation of Yeast Chromosome-Sized DNAs by Pulsed Field Gradient Gel Electrophoresis", Cell, vol. 37, pp. 67-75 (1984).
Carle et al., "Electrophoretic Separations of Large DNA Molecules by Periodic Inversion of the Electric Field," Science, vol. 232, pp. 65-68 (1986).
Chu et al., "Separation of Large DNA Molecules by Contour-Clamped Homogenous Electric Fields", Science, vol. 234, pp. 1582-1585 (1986).
D. Vollrath et al, Nucleic Acids Res., 15(19), 7865-7876, (1987).
G. F. Carle and M. V. Olson, Nucleic Acids Res., 12: 5647-5664, (1984).
K. Gardiner et al., Som. Cell Mol. Genet., 12: 185-195, (1986).

Primary Examiner—John F. Niebling
Assistant Examiner—Isabelle Rodriguez
Attorney, Agent, or Firm—Howson and Howson

[57] ABSTRACT

A method of separating DNA molecules by gel electrophoresis is disclosed which employs alternate application of high and low strength electric fields in opposite directions to a gel matrix containing DNA. The high strength field is maintained for a shorter interval than the low strength field, and the ratio of the product of the low strength field and its pulse interval to the product of the high strength field and its pulse interval is greater than 4:1 and sufficient to produce a net migration of the DNA molecules in the direction of the low strength field.

10 Claims, 3 Drawing Sheets

SEPARATION OF LARGE DNA MOLECULES IN ALTERNATING ASYMMETRIC ELECTRIC FIELDS

The research work which resulted in the invention described and claimed herein was sponsored by the United States Department of Health and Human Services.

The present invention relates generally to a method for separating large DNA molecules by electrophoresis. More particularly, the invention relates to the use of alternating high and low strength electric fields in opposite directions to allow separation by net migration of DNA molecules in the low field direction.

BACKGROUND OF THE INVENTION

Gel electrophoresis is a technique employed primarily in the fields of molecular biology and genetic engineering in which ions are separated by size as they migrate through a gel medium in response to an applied electric field. Various electrophoresis techniques have been employed in the qualitative analysis and separation, recovery and purification of mixtures of macromolecules, particularly mixtures of proteins, nucleic acids, and chromosomes.

Separation of DNA molecules up to about 20,000 base pairs, or 20 kb, in length is routinely achieved by placing DNA in an agarose gel and subjecting the molecules to a constant field. The electric field applies a constant force on the charged DNA molecules and separation is achieved through a length-dependent interaction with the gel matrix. This interaction causes the movement of longer DNA molecules to be retarded to a greater extent than smaller DNA molecules. However, the size of DNA molecules which can be separated by the standard technique is limited since all DNA molecules above about 50,000 base pairs migrate at substantially the same rate.

A variety of modifications of standard electrophoresis techniques have been devised to overcome the size threshold problem. One method of gel electrophoresis capable of separating DNA molecules up to about 2,000 kb in length alternately applies two approximately perpendicular electric fields. One of these fields is uniform and the other is variable. This causes the DNA to migrate along the diagonal in a stair step fashion making right angle turns at each pulse. Length-dependent separation of DNA molecules in the mixture originally applied to the gel is most probably achieved because small molecules turn corners more rapidly than larger molecules. This method results in curved and distorted DNA tracks. See, e.g., Schwartz, D. C. and Cantor, C. R., Cell, 37: 67–75 (1984).

Another improved electrophoresis technique was described by Carle, G. F. and Olson, M. V., Nucleic Acids Research, 12: 5647–5664 (1984). In this method alternate geometries for gel boxes and electrode arrays in an electrophoresis apparatus have been introduced to take advantage of the principle established by Schwartz, et al., supra. According to this method, electrophoresis is conducted by alternately applying two non-uniform electric fields that are approximately orthogonal. The result of using this technique is that the DNA gel tracks are symmetrical in pattern, but the outer tracks are strongly curved, making accurate size comparison difficult.

A more recent attempt to improve the geometry of the DNA tracks involves placing the gel in a vertical position and applying the alternating electric fields at an angle to the plane of the gel. See, e.g., Gardiner, K. et al., Som. Cell Mol. Genet., 12: 185–195 (1986). This approach produces linear DNA tracks by alternating the orientation of applied voltage by 90°. It is the frequency of this alteration which determines the size range of molecules to be resolved. The alternating electric fields are delivered in this method in equivalent pulses and the samples move straight down the lanes directly below the loading wells of the electrophoresis apparatus. However, because of the relatively large cross-sectional area for ion flow, a power supply must be used which is able to deliver relatively high currents at reasonable voltages of approximately 100 to 200 volts. This effectively limits the size of the gel that can be run to approximately $7 \times 10$ centimeters, or 70 square centimeters in area.

Another electrophoresis technique is described by G. Chu et al, Science, 234: 1582–1586 (1986). This electrophoresis technique is characterized by contour-clamped homogeneous electric fields. The electric fields in this method are arranged along a polygonal contour, and the electric field alternates between two orientations. A recent approach has also been described by Carle, G. F. et al in Science 232: 65–68 (1986). In this method, separation of large DNA molecules is achieved on a standard horizontal gel apparatus by alternately reversing the polarity of a uniform electric field in one dimension. Net forward migration of the DNA molecules is achieved by using a longer pulse time of a fixed voltage in the "forward" direction vs. a shorter pulse time at the same voltage in the "reverse" direction. Thus DNA migrates in the direction of the longer application of uniform voltage. Alternatively, these researchers obtained similar results by employing a constant pulse interval in combination with a higher electric potential in the forward direction and a lower electric potential in the reverse direction, the net DNA migration occurring in the direction of the greater voltage or potential.

There remains a need in the field of molecular biology for additional alternative approaches to electrophoretic separation of large DNA molecules.

BRIEF SUMMARY OF THE INVENTION

The present invention provides a novel gel electrophoresis method for separating DNA molecules. This method employs an asymmetric alternating electric field.

As a first step, an electric field of relatively low potential is applied in a first or forward direction for a stated pulse interval. The polarity is thereafter reversed and an electric field of much higher strength, approximately 2–20 fold higher strength, is applied in the opposite direction for another pulse period and the cycle is repeated. The relation of the low potential forward field to the high potential reverse field is defined as the ratio of the product of the low potential electric field and pulse interval in the forward direction to the product of the high potential electric field and pulse interval in the reverse direction. For the method of the present invention to operate, this first product of the ratio must be significantly larger than the second product. Thus, according to this method and in direct contrast to other electrophoresis techniques, net migration of DNA occurs in the low potential forward direction.

One aspect of the method uses a fixed time interval over the entire electrophoresis run and thus does not require changes in switching intervals. Other aspects of the method of the present invention employ fixed electric potentials and variable time intervals, or alternatively variable potentials and time intervals, provided that the ratio of the product of the low potential electric field and pulse time for the forward direction is significantly greater than that of the high potential and pulse time in the reverse direction.

The method employs a conventional 22×24 centimeter gel electrophoresis apparatus with the additional features of an electronic variable timer containing a double pole/double throw (DPDT) relay, and variable resistors to adjust field strength. These additional components, incorporated in an otherwise standard gel electrophoresis apparatus, control the duration, polarity and magnitude of the electric fields as provided by the novel method.

The advantages offered by the method of the present invention include the ability to separate molecules from about 0.15 to about 2000 kb. The method can employ standard 22×24 cm gel apparatus, and separate satisfactorily in a single run. Additionally, the DNA migrates in straight tracks on a horizontal gel apparatus, facilitating size comparisons. These and other advantages of the invention, as well as additional features will become apparent from the detailed description which follows.

DETAILED DESCRIPTION OF THE INVENTION

Figure 1:
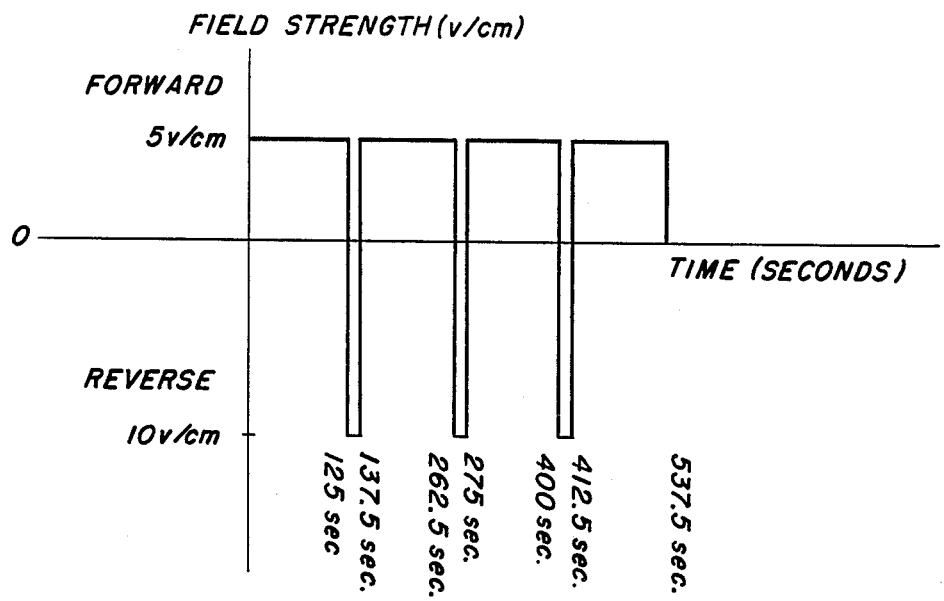
FIG. 1 is a graphical illustration of the electric field strength, direction and pulse time of the method of the invention.

The present invention provides a novel and improved gel electrophoretic method for the separation of DNA molecules by size and charge. The method employs alternating asymmetric electrical fields by applying, to DNA in a gel matrix, a low potential electric field in a first direction for a first predetermined pulse time interval. This first direction of low potential is the direction of net DNA migration according to this method. Hereinafter, the direction of net DNA migration shall be referred to as the "forward direction".

This step is followed by a reversal of the polarity of the electric field by 180° for a second predetermined interval. The potential of this "reverse" field is always greater than that for the forward field, but the second predetermined pulse time interval is significantly less than the first time interval. According to this method, the product of the low potential voltage and the pulse time interval in the forward direction is always significantly greater than the product of the high field voltage and high field pulse interval. Hereinafter, the ratio formed by the forward direction product (low voltage × forward pulse interval) to the reverse direction product (high voltage × reverse pulse interval) will be referred to as the "Method Ratio". Preferably the Method Ratio is at least 4:1. The upper limit of the Method Ratio depends upon the size of the DNA fragments to be separated, but can be as great as 1000:1. A preferred range of the Method Ratio is between about 4:1 to about 20:1.

These two steps are repeatedly alternated. During the application of these steps, the direction of buffer flow across the electrophoresis gel is constant in the reverse direction, i.e., opposite the direction of net DNA migration. Repetition of the steps of the method of the present invention may be continued for a sufficient time period dependent on the mass of the DNA molecules in the sample undergoing gel electrophoresis. Depending on such samples, the total time period to perform the method of the present invention or electrophoresis "run" may be between 2 hours to 150 hours. According to this method, shorter DNA molecules in the matrix migrate further in the first low potential direction than do larger DNA molecules, providing for clear separation of molecules by size on the gel. All DNA undergoes net migration in the forward direction.

Although it has previously been found that DNA molecules above a certain molecular weight migrate at the same rate in agarose gels, one possible theoretical explanation underlying the separation method of the present invention is that in the high field direction DNA molecules are forced into an elongated confirmation and move backward at a similar rate regardless of size. However, when the polarity is reversed and field strength is lowered, the time required to change from high to low field conformation and move in the opposite direction becomes strongly dependent on length or molecular weight. When the polarity is again reversed, the molecules reorient more rapidly under the high field strength condition and again move backward at similar rates. Thus, a ratcheting effect is produced in which DNA molecules of different sizes move backward the same distance in the high field direction but then move forward at a distance that is dependent on the length of the DNA molecule in the low field direction.

The term "pulse time interval" refers to the time interval over which one of the electrical fields is on (or high) while the other one is off (or low). According to one aspect of the invention, where the forward and reverse fields are fixed, the pulse intervals for the forward and reverse direction electric potentials may vary over the duration of the electrophoresis run, becoming greater in duration as the gel run is longer, within the parameters of the Method Ratio. Alternatively, the pulse intervals may be fixed for the electrophoresis run and the forward and reverse direction voltages may vary within the Method Ratio. In still other aspects of this electrophoresis method, the pulse intervals and forward and reverse voltages may be all variable or all fixed, provided that the Method Ratio remains preferably within the 4:1 to 1000:1 limits.

Pulse time intervals for use in the method of the present invention have successfully been used as low as 60 seconds and as high as 150 seconds for the low potential forward directed electrical field and as low as 6 seconds and as high as 17.5 seconds for the high potential or backward electrical field.

The low potential electrical field is desirably applied in a range of between 1–6 volts per centimeter of gel matrix. The high potential electric field may be desirably applied in a range of between 5–25 volts per centimeter of gel matrix. The ratio of the reverse (high voltage) to forward (low voltage) potential can desirably range from 2:1 to 20:1.

It is expected that the method of the invention will also be applicable, using wider ranges of pulse time intervals and electric potentials, depending on the mass of DNA or other composition in the sample to be electrophoresed.

FIG. 1 illustrates the application of the method of the present invention in graphical form, showing the relationships between forward and reverse directions of the electrical fields, field strength and pulse interval for the method. The parameters selected for this graph are illustrative only. The X axis is FIG. 1 plots the time component, showing duration of the pulses of applied electrical force. This axis also represents the division between the forward and reverse directions of the electrical force. The Y axis illustrates the strength of the electrical field potential in both directions. Thus, the force applied initially is in the forward direction at 5 v/cm for a pulse time interval of 125 seconds, followed by a force applied in a reverse direction of 10 v/cm for 12.5 seconds. The Method Ratio of this illustration is 5 v/cm×125 s :10 v/cm×12.5s, or 5:1. These same force pulses are applied alternatively according to the method, as shown in the graph of FIG. 1.

An additional aspect of the method of the present invention involves proper cooling of the agarose gel by the buffer flow in the electrophoresis apparatus during performance of this method. In this method the direction of buffer flow is always in a direction opposite to that of net DNA movement in the electric field. Because of electrical resistance, the buffer gets warmer as it passes by the gel, establishing a temperature gradient in the gel. The DNA subjected to either the forward or reverse electric field runs counter to this gradient, moving from a warmer to a cooler area in the gel. The trailing edge of a DNA band runs faster than the leading edge, thereby compressing it. In this method it is desirable for the buffer to flow at a rate that allows a temperature gradient ranging from 8°–9° centigrade to 13°–14° centigrade to be established across the length of the gel box.

Figure 2:
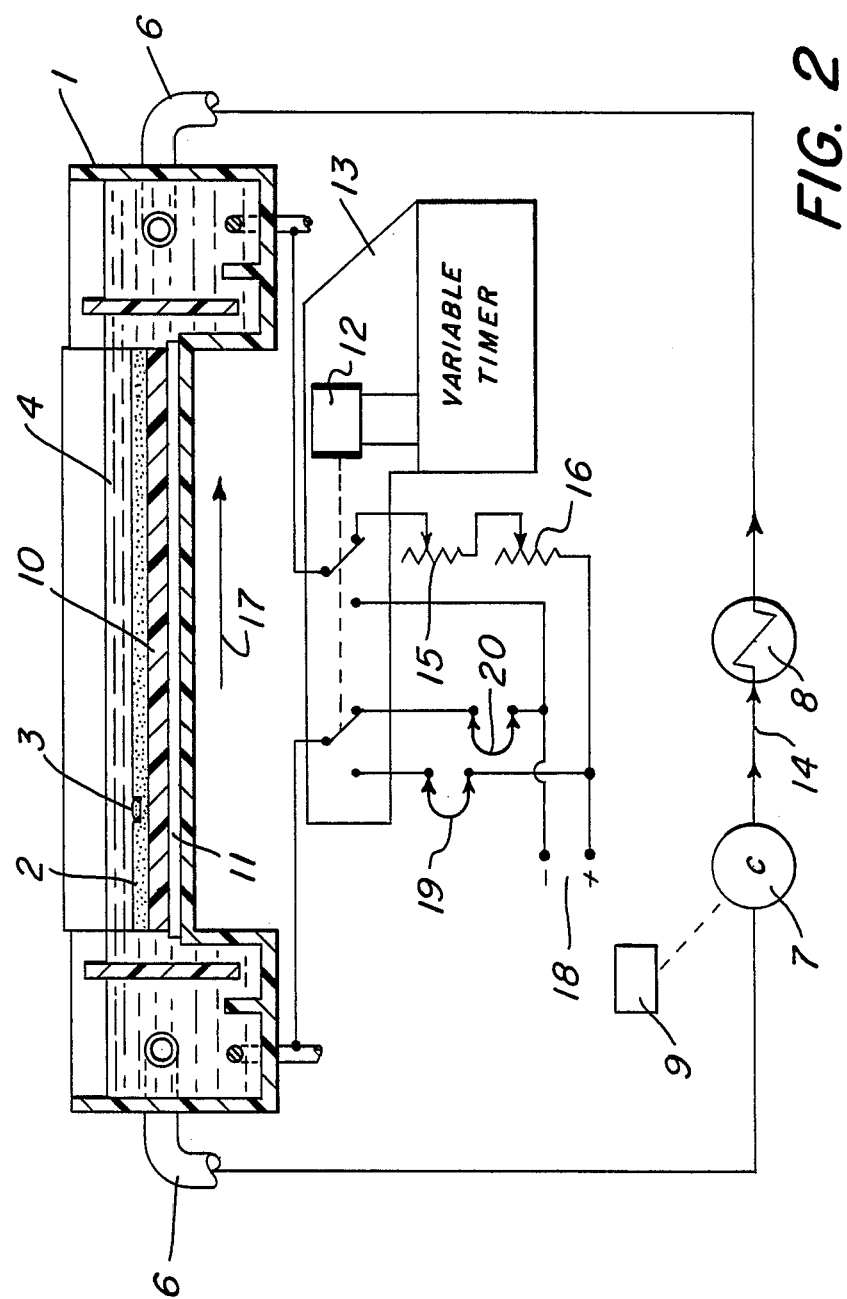
FIG. 2 is a longitudinal section of a gel electrophoresis apparatus employed in the method of the present invention with associated electrical components shown schematically.

A laboratory device useful in explaining certain principles of the invention is illustrated in FIG. 2, partly in longitudinal section and partly in schematic form.

The alternating asymmetric electrical field method of the present invention may be run in a conventional, horizontal gel electrophoresis apparatus as shown in FIG. 2 (e.g. BRL model H1). The gel box 1 is a commercially available component, generally made of acrylic polymer or similar electrically non-conductive material. Inside the gel box the agarose gel sheet 2 is situated on a flat gel support 10. A small sample 3 (approximately 3 mm in depth) of the material to be separated is placed in a small rectangular depression in the gel sheet. Multiple depressions can be provided side-by-side in the gel sheet so that a number of separations can be carried out simultaneously in the gel box. A buffer 4, conventional for electrophoresis, fills the gel box, extending over the gel approximately 1 mm in depth.

A conventional buffer can be 45 mM Tris (hydroxymethyl) aminomethane, 45 mM boric acid and 0.5 mM ethylenediamine tetraacetic acid (EDTA). The buffer 4 circulates through a tube 6 which is connected to a circulating pump 7 and ice bath 8. The pump is operated by motor 9. In FIG. 2., the buffer flow, is opposite the direction of migration of DNA, as indicated by the arrows 14, moving from right to left across the gel.

To allow for adequate cooling beneath the gel as well as above it by the buffer, glass rods 11 are placed parallel to one another beneath the agarose gel support 10. These rods extend longitudinally in the gel box with their long axis parallel to the direction of net migration. The size of the rods is not critical. In the example below, rods of approximately 2 mm in diameter and 25 cm in length, were employed in the electrophoresis apparatus. The buffer height is adjusted so that 1 mm of liquid is above the gel. This arrangement allows buffer to flow above and below the gel, as indicated in FIG. 2. A current of 100–150 milliamperes, to the motor 9 is sufficient to establish a flow rate of approximately 120 mls/minute through ice bath 8, and set up the appropriate temperature gradient. The D. C. power supply, indicated generally at 18, is also a conventional, commercially available item for an electrophoresis apparatus (e.g. Heathkit model SP-2717).

The heart of the switching circuit of FIG. 2 is the variable timer 13. One commercially available unit is Eagle Signal model number DA100, manufactured by Eagle Signal Controls of Texas. Timer 13 operates internal D.P.D.T. relay 12, which controls the reversal of the electric field applied to the electrophoresis apparatus. The timer and relay combination, with associated circuitry and controls, enables the user to control the duration, polarity and magnitude of the applied pulses. It is the ability to vary these parameters that makes possible the separation of large molecular weight DNA molecules according to the present method.

Timer 13 also includes user-adjustable timers which independently set the duration of both forward and reverse pulses. The action of timer 13 and internal relay 12 combination enables the reversal of the field applied to the gel. Control of the magnitude of the field applied to the gel is obtained by use of variable resistors 15 and 16, which preferably have a resistance range from 0 to 50,000 ohms, or from 0 to 5,000 ohms, respectively. Additional resistors can be substituted for jumpers 19 and 20 to add increased resistance on this system, if desired. Adjustment of resistors 15 and 16 enables control of the current actually applied to the gel, and thus the magnitude of the forward and reverse electric fields. Adjustment of 50 k resistor 15 and 5 k resistor 16, together with adjustment of the voltage of power supply 18, is sufficient to establish forward and reverse field ratios suitable for most applications. In FIG. 2, the direction of the low voltage electric potential is indicated at arrow 17.

Figure 3:
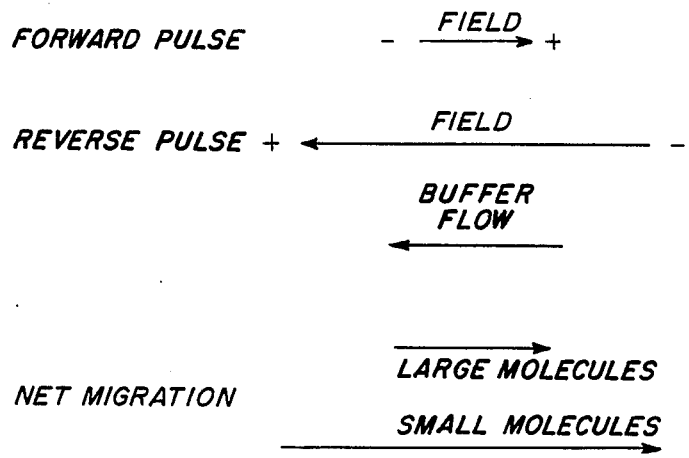
FIG. 3 is a graphical illustration of the operation of the method of the present invention showing directions of electric field and net migration of DNA molecules.

The overall functioning of the method of the invention is illustrated by the schematic of FIG. 3. The forward pulse or forward application of a low potential electric field is illustrated as a small arrow pointing right from the negative electrode to the positive electrode. The reverse pulse shows the electric field of higher potential by a longer arrow pointing from the negative electrode to the positive electrode. The arrow between the forward and reverse voltage arrows, shows that the buffer travels across the gel in the reverse direction, opposite the direction of net DNA migration. The net result of this method is illustrated by two arrows, pointing in the direction of the forward pulse. One arrow, representing net migration of larger DNA molecules, is shorter than the other arrow, representing net migration of smaller molecules. Thus, according to the method, the smaller molecules migrate further in the forward direction than do the larger molecules.

The novel electrophoretic method disclosed herein has a number of applications in the genetic engineering or molecular biology area. As one example, this electrophoretic method may be used for resolving a large number of bands in a single gel from a mixture of DNA. This is an important consideration when eukaryotic DNA is analyzed. Similarly, electrophoresis may be used to perform chromosome mapping or separation and karyotyping of chromosomes, particularly of large DNA molecules, such as eukaryotic chromosomes, e.g. yeast, trypanosomes. The method may also be used to assess the effect of radiation or various chemical agents or drugs on chromosomes (e.g. chromosome damage and DNA breakage) nucleic acids and proteins because of the ability to separate such materials as provided by the method of the invention. This method may also be used for convenient production of gene libraries. Similarly, polymers can be accurately and quickly analyzed for molecular weight, distribution, branching and other physical properties by this method.

The following examples illustrate certain aspects of the novel method of the present invention. Without limiting the invention in scope, the DNA employed in the sample is yeast chromosomal DNA; however, one of skill in the art will acknowledge the applicability of this method to DNA from a variety of sources, other compositions appropriate for electrophoretic separation, and for a variety of known uses of an electrophoretic method.

EXAMPLE

Preparation of Yeast DNA

The yeast S. cerevisiae strain Kt458, provided by K. Tachell, was grown to stationary phase at 30° C. in 25 ml of YPD medium. One gram yeast extract, 2 g dextrose, and 2 g bactopeptone were added to 100 mls of distilled water. High molecular weight DNA was prepared by the method of Schwartz and Cantor, supra, in which the cells are first suspended in solid agar and then lysed. Yeast cells were washed twice at 0° C. with 10 ml of 0.05 M EDTA/ 1 mM tris, pH 7.8 and resuspended at a density of $1 \times 10^8$ cells/ml in the same buffer at 42° C. containing 1% agarose (Seakem GTG). Seventy mg/ml lyticase (900 units/ml, Sigma) was added to the cell suspension, mixed, pipetted into 3 mm diameter tubes and allowed to cool to room temperature. Plugs were incubated 48 hrs. in 50 ml of SB buffer (0.5 M EDTA/0.01 M tris ph 7.5) at 37° C. followed by 48 hours in 50 ml DSP buffer (0.5 M EDTA, 0.01 tris, pH 7.5, 1% sarkosyl, 1 mg/ml proteinase K) at 50° C. Plugs are stored in SB buffer and dialysed against 0.5 TBE buffer before use.

Separation of Yeast DNA

Yeast DNA as prepared above was electrophoretically separated using the method of the present invention. The gel (1.0%) was cast and run in 0.5× buffer composed of 45 mM Tris pH, 45 mM Boric Acid 7.8, 0.5 mM EDTA)(TBE) and 0.5 ug/ml ethidium bromide in a large gel box (gel 22×24×0.5 cm) [Bio Res. Labs] The pulse intervals were 125 sec. at 5 v/cm. in the forward direction and 12.5 sec. at 10 v/cm. in the reverse (high field) direction. The Method Ratio was 5:1. The gel was run approximately 28 hours. Forward direction is defined as the direction in which the DNA migrates.

Yeast DNA electrophoresced according to the method of the invention described above yielded 10 bands. Using a 1.5% gel and 15 second high field pulse (Method Ratio of 4.17:1), a second run on the bands according to this method resolved bands 1-2 and 7-8 into two bands each. Thus a minimum of 12 bands were separated by the method. This DNA was transferred to a nitrocellulose membrane and hybridized using conventional techniques with a DNA probe containing DNA sequences specific for yeast chromosomes I, IV, and XV. This probe hybridized to bands 1,2, 11 and 12. Using probes specific for single chromosomes, bands 1,12 and 11 were found to contain DNA from yeast chromosome I, (approximately 260 kb), chromosome IV (approximately 1600 kb) and chromosome XV (approximately 1200 kb), respectively. Thus, this separation method of the invention resolves DNA fragments from 260 kb to greater than 1600 kb bp.

Figure 4:
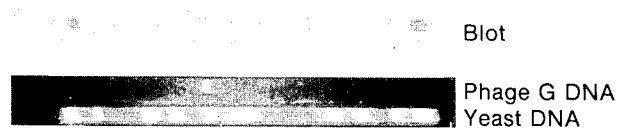
FIG. 4 is a schematic of a gel illustrating separation of yeast DNA by the method of the invention.

FIG. 4 illustrates a electrophoresis gel according to the present invention.

Other experiments employing the method of the present invention have employed electric potentials, pulse time intervals and durations different from those disclosed in the Examples, and demonstrate the applicability of this method for a variety of uses. For example, a forward electric potential as low as 5 v/cm for a pulse time interval of 75 seconds with a reverse electric potential of 10 v/cm for 5 seconds (Method Ratio of 7.5:1) has proven capable of separating DNA for a duration of 40 hours. Other low and high field potentials, pulse time intervals and durations which have been used in this method included forward: 5 v/cm for 150 seconds and reverse: 10 v/cm for 15 seconds (Method Ratio of 5:1) for 50 hours.

It is expected that a wide range of electric potentials, pulse time intervals and total electrophoresis durations, as well as a variety of electrophoresis apparatus arrangements, may prove useful in the practice of the present invention to provide the net effect of separating DNA molecules by causing migration in the direction of the low potential electric field by the application of asymetric alternating electric fields of the present invention. Additionally, it is expected that the method of the present invention may be employed with compositions other than DNA molecules, e.g. polymers, enzymes and the like. Such numerous modifications and variations of the present invention are expected to be employed by those of skill in the art. These modifications are intended to be encompassed by the appended claims.

What is claimed is:

1. A method for separating DNA molecules by gel electrophoresis comprising:
    alternately applying to DNA in a gel matrix a first potential electric field in a forward direction for a first time interval; and a second potential electric field always greater in magnitude than said first field in a second 180° reverse direction for a second time interval less than said first interval, wherein the ratio of the product of said first potential electric field and said first interval to the product of said second potential electric field and said second interval is sufficient to cause shorter DNA molecules in said matrix to migrate further in said first direction than do longer DNA molecules.

2. The method according to claim 1 wherein said ratio is at least 4:1.

3. The method according to claim 1 wherein said ratio is 1000:1.

4. The method according to claim 1 wherein said ratio is between 4:1 to about 20:1.

5. The method according to claim 1 wherein said first electric field is applied in a range of about 1 to about 6 volts per cm of gel matrix said second electric field always being greater in magnitude than the magnitude of said first field.

6. The method according to claim 1 wherein said second electric field is applied in a range of about 5 to about 25 volts/cm gel matrix said first electric field always being lesser in magnitude than the magnitude of said second field.

7. The method according to claim 1 wherein said first time interval is in the range of 60 to about 800 seconds.

8. The method according to claim 1 wherein said second time interval is applied in a range of about 6 to about 60 seconds.

9. The method according to claim 1 wherein said repetitive steps are continued for between about 2 to about 150 hours.

10. The method according to claim 1 wherein said DNA molecules range in size from about 0.15 to about 2000 kb pairs.

* * * * *